United States Patent [19]

Perry

[11] 4,161,425

[45] Jul. 17, 1979

[54] ENZYMATIC REAGENT SYSTEM FOR TOTAL CHOLESTEROL ASSAY USING OXYGEN-RATE METHOD

[75] Inventor: Andrew W. Perry, Anaheim, Calif.

[73] Assignee: Beckman Instruments, Inc., Fullerton, Calif.

[21] Appl. No.: 778,919

[22] Filed: Mar. 18, 1977

Related U.S. Application Data

[63] Continuation-in-part of Ser. No. 701,919, Jul. 1, 1976, abandoned.

[51] Int. Cl.$^2$ ............................................. G01N 31/14
[52] U.S. Cl. ...................................................... 435/11
[58] Field of Search ................. 195/99, 103.5 R, 127; 252/408 R; 23/230 B, 230 R

[56] References Cited

U.S. PATENT DOCUMENTS

| | | | |
|---|---|---|---|
| 3,857,771 | 12/1974 | Sternberg | 204/195 B |
| 3,884,764 | 5/1975 | Goodhue et al. | 195/103.5 R |
| 3,907,645 | 9/1975 | Richmond | 195/103.5 R |
| 3,933,593 | 1/1976 | Sternberg | 195/103.5 R |

FOREIGN PATENT DOCUMENTS

| | | | |
|---|---|---|---|
| 2229966 | 12/1974 | France | 23/230 B |
| 2254026 | 7/1975 | France | 195/99 |

OTHER PUBLICATIONS

Richmond, "Preparation and Properties of a Cholesterol Oxidase from Nocardia sp. and its Application to the Enzymatic Assay of Total Cholesterol in Serum", Clin. Chem., vol. 19, (1973) pp. 1350-1356.

Flegg, "An Investigation of the Determination of Serum Cholesterol by an Enzymatic Method", Ann. Clin. Biochem, vol. 10, (1973) pp. 79-84.

Hernandez et al., "Purification and Properties of Pancreatic Cholesterol Esterase," J. Biol. Chem., vol. 228 (1957) pp. 447-457.

Hyun et al., "Purification and Properties of Pancreatic Juice Cholesterol Esterase," J. Biol. Chem. vol. 244 (1969) pp. 1937-1945.

Allain et al., "Enzymatic Determination of Total Serum Cholesterol," Clin. Chem., vol. 20 (1974), pp. 470-475.

Turfitt, "The Microbiological Degradation of Steroids," Biochem. J., vol. 39 (1944) pp. 492-496.

Schatz et al., "The Ability of Soil Microorganisms to Decompose Steroids," J. Bacteriol. vol. 58, (1949) pp. 117-125.

Stadtman et al., "Studies on the Microbiological Degradation of Cholesterol, " J. Biol. Chem., vol. 206 (1954) pp. 511-523.

Richmond, "The Development of an Enzymic Technique for the Assay of Cholesterol in Biological Fluids," i Scand. J. of Clin. Lab. Invest., vol. 29, Suppl. 26, Abstract 3.25 (1972).

Nekhorosheva, "Use of Semiliquid Nutritional Media in the Study of Bactericidal Activity of Cationic Surface-Active Agents," Chem Abstracts, vol. 82, No. 21 (1975), p. 84 nbs. No. 133462s.

Karger et al., An Introduction to Separation Science, John Wiley & Sons, New York, (1973), pp. 431-433.

Primary Examiner—Thomas G. Wiseman
Attorney, Agent, or Firm—Robert J. Steinmeyer; Robert S. Frieman

[57] ABSTRACT

A novel enzymatic reagent system is provided for assaying for total cholesterol in a liquid containing cholesterol, cholesterol esters, oxygen and substances which appear to inhibit the reactions between the enzymes and cholesterol and/or cholesterol esters. The novel reagent system comprises an aqueous solution of a buffering agent, cholesterol oxidase, cholesterol esterase, and a cationic surfactant in an amount sufficient to neutralize the effect of the inhibiting agents.

27 Claims, No Drawings

ENZYMATIC REAGENT SYSTEM FOR TOTAL CHOLESTEROL ASSAY USING OXYGEN-RATE METHOD

CROSS REFERENCES TO RELATED APPLICATIONS

This application is a continuation-in-part of Applicant's prior copending application, Ser. No. 701,919, filed July 1, 1976, now abandoned.

BACKGROUND OF THE INVENTION

1. Field of the Invention

The instant invention pertains to cholesterol assay enzymatic reagents containing cholesterol oxidase.

2. Description of the Prior Art

Present enzymatic reagents using cholesterol oxidase to measure cholesterol in a specimen measure the amount of hydrogen peroxide produced by the reaction between oxygen and cholesterol which is translated into a measure of the amount of cholesterol in the specimen. The hydrogen peroxide measurements are generally based upon the reaction between hydrogen peroxide and a dye which causes a change in color. This change of color is measured and is translated into a measurement indicating the quantity of hydrogen peroxide present.

Reducing substances, such as glutathione, ascorbic acid and uric acid which are present in human fluids, react with hydrogen peroxide and prevent all of the hydrogen peroxide from reacting with the dye. This results in a loss of accuracy in the cholesterol assay.

One solution to this problem is to measure the rate of consumption of oxygen in enzymatic conversion of cholesterol to cholest-4-en-3-one and hydrogen peroxide and to translate the measurement into the amount of cholesterol present. An oxygen rate analyzer and method providing such a measure are described in U.S. Pat. Nos. 3,857,771 and 3,933,593 to James C. Sternberg, said patents being incorporated herein in toto by reference.

While oxygen rate measuring systems, such as described in the aforesaid Sternberg patents, may be usefully employed to measure total cholesterol in a specimen, the presence of substances in the specimen which inhibit the reaction of enzymes with cholesterol and/or cholesterol esters or which inhibit the availability of cholesterol for reaction with the enzymes (hereinafter referred to collectively as inhibiting agents) may render such measurements rather inaccurate. In particular, inhibiting agents which appear to be present in turbid serum containing above normal concentration of triglycerides appear to decrease the availability of reactable cholesterol and/or decrease the rate at which the enzymes catalyze reactions leading to the consumption of oxygen (hereinafter referred to collectively as the oxygen consumption inhibiting effects). In either event, the result is a reduction from the normal rate of consumption of oxygen such that the measurement of the rate of oxygen consumption in the presence of such inhibiting agents does not yield an accurate measure of cholesterol concentration. For example, it has been found that when using the oxygen rate measuring system to determine the total cholesterol level in certain specimens, the rate of oxygen consumption was lower than would be expected from the cholesterol content of the specimen, the actual cholesterol content of the specimen having been previously determined by the well accepted assay for total cholesterol of Abell et al., *J. Biol. Chem.*, 195:367 (1952), said article being incorporated herein in toto by reference.

SUMMARY OF THE INVENTION

It has been discovered that by the addition of a cationic surfactant to a cholesterol assay enzymatic reagent, of the type comprising cholesterol oxidase and a buffering agent, the rate of oxygen consuming reactions is substantially unaffected by the presence of the aforesaid inhibiting agents in the specimen being assayed. As a result, the rate of oxygen consumption measured by oxygen rate analyzers such as described in the Sternberg patents may be accomplished in a matter of seconds and will be a true measure of the total cholesterol contained in the specimen being analyzed.

In order to avoid subjecting the specimen to a separate saponification procedure, it is preferred that the cholesterol assay enzymatic reagent further comprise cholesterol esterase. It is believed that cholesterol esterase catalyzes the reaction between water and cholesterol esters present in the specimen to yield cholesterol and a fatty acid by-product. The cholesterol produced by cholesterol esterase and any cholesterol initially present in the specimen are reacted with oxygen by the catalytic action of the cholesterol oxidase to yield cholest-4-en-3-one and hydrogen peroxide. The rate at which oxygen is consumed in the reaction with cholesterol may be translated by known techniques into a measure of the cholesterol concentration.

DESCRIPTION OF THE PREFERRED EMBODIMENTS

The cholesterol assay enzymatic reagent of the instant invention comprises cholesterol oxidase, a buffering agent in an amount to produce a solution having a pH of between about 5.5 and about 8, and a cationic surfactant in an amount sufficient to neutralize substantially all oxygen consumption effects of inhibiting agents present in a sample to be assayed. Preferably, the reagent also comprises cholesterol esterase.

The cationic surfactants employed in the instant invention are used in amount sufficient to neutralize the oxygen consumption inhibiting effects of the triglycerides and other inhibiting agents. One method of determining the minimum and maximum quantities, and therefore the range, of cationic surfactant suitable for use in the cholesterol assay enzymatic reagent is as follows. The amount of total cholesterol in a series of specimens are first determined by a reference method, such as that of Abell et al., supra, said article having been incorporated herein in toto by reference. The total cholesterol values of said series of specimens are then determined by using the oxygen rate method (such as described in U.S. Pat. Nos. 3,933,593 and 3,857,771, said patents having been incorporated herein in toto by reference) in conjunction with a set of enzymatic reagents within the scope of the instant invention, such as Examples I to VIII, infra, wherein the members of said set contain various quantities of the cationic surfactant. The minimum quantity of cationic surfactant required is that amount which gives total cholesterol values for all the specimens which values are equal to those values obtained by the reference method. (As discussed above, at sub-minimum levels of cationic surfactant, the total cholesterol values for certain specimens appear lower than the reference method.)

When the cationic surfactant is present in an amount greater than the maximum amount desirable, surfactant denaturation of the cholesterol oxidase and cholesterol esterase enzymes occurs. Surfactant denaturation results in the retardation of both the rate of conversion of cholesterol esters to cholesterol and the rate of conversion of cholesterol to cholest-4-en-3-ol. As the quantity of cationic surfactant increase above this maximum amount, the reaction's rate of oxygen consumption becomes slower and slower until it becomes impractical to measure said rate.

In addition to the above, it is preferred that the enzymatic reagent of the instant invention comprise from about 0.01 to about 0.4 and more preferably from about 0.05 to about 0.2 percent by weight of the final solution of cationic surfactant. Optimally, said reagent comprises 0.1 percent by weight of said cationic surfactant.

Virtually any cationic surfactant can be employed in the instant invention. A compilation of commercially available cationic surfactants which can be used in the instant invention appears in McCutcheon's Detergents & Emulsifiers, 1975, North American Edition, McCutcheon Division, MC Publishing Co., Glen Rock, N.J., said publication being incorporated herein in toto by reference. Quaternary imidazolinium, pyridinium, quinolinium, and quaternary ammonium cationic surfactants are all suitable for use in the instant invention. Typical of the cationic surfactants which are particularly useful in the present invention are $\beta$-hydroxyethylbenzyl stearyl imidazolinium chloride, laurylpyridinium chloride, and laurylisoquinolinium bromide. Further, cationic quaternary ammonium surfactants including di isobutylphenoxyethyoxyethyl dimethyl benzyl ammonium chloride, di isobutylcresoxyethoxyethyl dimethyl benzyl ammonium chloride and methyldodecylbenzyl trimethyl ammonium chloride appear to be a preferred class of cationic surfactants. More specifically, alkyldimethylbenzylammonium salts are a preferred class of cationic quaternary ammonium surfactants.

The particular alkyldimethylbenzylammonium salts which are used in preferred embodiments of the invention are Hyamine 3500 manufactured by Rohm and Haas Company of Philadelphia, Pennsylvania, and Zephiran Chloride manufactured by Winthrop Laboratories, a division of Sterling Drug Company of New York City. Hyamine 3500 is a trade name for sodium alkyldimethylbenzylammonium chloride wherein the alkyl group is a mixture of alkyls containing about 50% of $C_{14}H_{29}$, about 40% of $C_{12}H_{25}$, and about 10% of $C_{16}H_{33}$. Zephiran Chloride is a trade name for alkyldimethylbenzylammonium chloride wherein the alkyl group is a mixture of alkyls from $C_8H_{17}$ to $C_{18}H_{37}$.

Any buffering agent compatible with the other constituents of the reagent is suitable for use therein. Exemplary of buffering agents which may be used are phosphate salts such as potassium orthophosphate, citrate salts such as sodium citrate, or acetate salts such as sodium acetate. The buffering agent is present in an amount to produce a solution having a pH of between about 5.5 to about 8 and preferably a pH of about 6.

Any cholesterol oxidase can be used in the reagent of the present invention. The exact amount of cholesterol oxidase employed in the reagent is not critical. Preferably, from about 0.2 to about 5, more preferably from about 0.5 to 2, and even more preferably from about 1 to about 1.5, International Units per milliliter of reagent of cholesterol oxidase is employed in the instant invention.

Optionally, about 1.2 International Units per milliliter of reagent of cholesterol oxidase is employed.

Any cholesterol esterase can be used in the instant invention. The exact amount of cholesterol esterase employed in the instant invention is not critical. From about 0 to about 5, preferably from about 0.001 to about 1, and more preferably from about 0.005 to about 0.05, International Units per milliliter of reagent of cholesterol esterase is employed in the present invention. Optimally, about 0.014 International Units per milliliter of reagent of cholesterol esterase is used.

In a preferred embodiment, a non-ionic surfactant is used to maintain the cholesterol and cholesterol esters of the serum of solution. When employed in the reagent of the instant invention, the amount of non-ionic surfactant used is not critical but is preferably present in an amount of from about 0.01 to about 0.5, more preferably about 0.05, percent by weight of the reagent. Virtually any non-ionic surfactant can be employed in the instant invention. A compilation of commercially available non-ionic surfactants which can be used in the instant invention appears in McCutcheon's Detergents & Emulsifiers, 1975, North American Edition, supra, said publication having been incorporated herein in toto by reference. Exemplary non-ionic surfactants which may be employed in the instant invention are nonylphenoxypolyethyleneoxy ethanol and polyoxyethylated sorbitol monolaurate.

Satisfactory results have been obtained using the non-ionic surfactant Triton X-100 in an amount of about 0.05 percent by weight of the total solution. Triton X-100 is a brand name for isooctylphenoxypolyethoxyethanol.

It is also preferred to add to the reagent system of the instant invention a bile salt. When employed in the reagent of the instant invention, the amount of bile salt used is not critical but is preferably present in amounts of about 0.01 to about 0.1, more preferably about 0.08, percent by weight of total solution. Bile salts appear to maintain cholesterol esters and cholesterol in a soluble condition and thus make them available for reaction by the enzymes. Exemplary of bile salts suitable for use in the reagent are sodium cholate, taurocholate, deoxycholate and taurodeoxycholate. In the preferred embodiment, sodium cholate is the preferred bile salt.

The following are compositions of preferred reagent systems of the present invention:

EXAMPLE I

| | |
|---|---|
| Cholesterol Esterase | 0.007 IU/ml |
| Cholesterol Oxidase | 1 IU/ml |
| $K_2HPO_4$ and $KH_2PO_4$ mixed to produce a solution pH of 6.0 | 1.0 molar |
| Triton X-100 | 0.05% |
| Sodium Cholate | 0.08% |
| Hyamine 3500 | 0.1% |

EXAMPLE II

| | |
|---|---|
| Cholesterol Esterase | 1 IU/ml |
| Cholesterol Oxidase | 1 IU/ml |
| $K_2HPO_4$ and $KH_2PO_4$ mixed to produce a solution pH of 6.0 | 1.0 molar |
| Sodium Cholate | 0,08% |

| | |
|---|---|
| -continued | |
| Hyamine 3500 | 0.08% |

EXAMPLE III

| | |
|---|---|
| Cholesterol Esterase | 1 IU/ml |
| Cholesterol Oxidase | 1 IU/ml |
| $K_2HPO_4$ and $KH_2PO_4$ mixed to produce a solution pH of 6.0 | 1.0 molar |
| Triton X-100 | 0.05% |
| Sodium Taurocholate | 0.08% |
| β Hydroxyethylbenzyl Stearyl Imidazolinium chloride | 0.1% |

EXAMPLE IV

| | |
|---|---|
| Cholesterol Esterase | 1 IU/ml |
| Cholesterol Oxidase | 1 IU/ml |
| Citric acid and sodium Citrate mixed to produce a pH of 6.0 | 1.0 molar |
| Triton X-100 | 0.5% |
| Hyamine 3500 | 0.1% |
| Sodium Cholate | 0.08% |

EXAMPLE V

| | |
|---|---|
| Cholesterol Esterase | 0.014 IU/ml |
| Cholesterol Oxidase | 1 IU/ml |
| Citric acid and sodium Citrate mixed to produce a pH of 6.0 | 1.0 molar |
| Laurylpyridinium Chloride | 0.1% |
| Sodium Cholate | 0.08% |

EXAMPLE VI

| | |
|---|---|
| Cholesterol Esterase | 1 IU/ml |
| Cholesterol Oxidase | 1 IU/ml |
| Acetic acid and sodium Acetate mixed to produce a pH of 6.0 | 1.0 molar |
| Hyamine 3500 | 0.1% |
| Polyoxyethylated Sorbitol Monolaurate Sodium | 0.05% |

EXAMPLE VII

| | |
|---|---|
| Cholesterol Esterase | 1 IU/ml |
| Cholesterol Oxidase | 1 IU/ml |
| Acetic acid and sodium Acetate mixed to produce a pH of 6.0 | 1.0 molar |
| Hyamine 3500 | 0.08% |
| Triton X-100 | 0.05% |
| Sodium Taurocholate | 0.08% |

EXAMPLE VIII

| | |
|---|---|
| Cholesterol Esterase | 0.014 IU/ml |
| Cholesterol Oxidase | 1.2 IU/ml |
| $K_2HPO_4$ and $KH_2PO_4$ mixed to produce a solution pH of 6.0 | 1.0 molar |
| Triton X-100 | 0.05% |
| Sodium Cholate | 0.08% |
| Hyamine 3500 | 0.1% |

Other examples of preferred reagent systems are as set forth in Example I replacing Hyamine 3500 with about 0.1 percent by weight of any one of the cationic and cationic quaternary ammonium surfactants previously listed herein.

The preferred reagent systems described herein employ cholesterol esterase to hydrolyze cholesterol esters into cholesterol. The invention, however, is not limited to cholesterol esterase to accomplish this hydrolysis but comprehends reagents employing other hydrolysis agents such as alkaline materials which may be substituted for cholesterol esterase. Exemplary of such alkaline materials are potassium hydroxide in ethanol and sodium hydroxide in ethanol.

If an alkaline material is substituted for cholesterol esterase to effect the hydrolysis of cholesterol esters, the serum must first be reacted with the alkaline material. An aliquot would then be reacted with a reagent system similar to the examples except that the reagent system would contain no cholesterol esterase.

The reagent system of the instant invention as described herein may be prepared as a single reagent containing all of the constituents described hereinabove or may be prepared as a kit consisting of two or three reagents. In preparing a reagent kit comprising two reagents, one reagent will contain cholesterol esterase and cholesterol oxidase, and the remaining reagent will contain the buffered solution and any other ingredients as discussed hereinabove. In preparing a reagent kit consisting of three separate reagents, a first reagent is comprised of a solution of cholesterol oxidase, a second reagent is comprised of cholesterol esterase, and a third reagent is comprised of an aqueous solution of buffer, surfactant, and any other ingredients described hereinabove.

The reagent system of the preferred embodiment is a kit consisting of two separate reagents because it is believed that the shelf life of the reagent system will be extended if the enzymes and remaining components of the reagent are separated from each other until ready for use. This should prevent the possibility of any reactions occurring among the constituents of the reagent system if they are mixed together and allowed to stand for prolonged periods of time prior to use.

The reagent system of the present invention may be stored and used in the form of an aqueous solution or the solution may be freeze dried by conventional means and reconstituted with deionized water when ready for use. The reagent system may also be prepared using the constituents thereof in powdered form which are solubilized with water when ready for use.

While particular embodiments of the invention chosen herein for purposes of a disclosure are at present considered to be preferred, it is to be understood that the invention is intended to cover all changes and modifications in the disclosed embodiments which fall within the spirit and scope of the invention.

The embodiments of the invention in which an exclusive property or privilege is claimed are defined as follows:

1. A cholesterol assay enzymatic reagent for rate determination of cholesterol in a sample to be assayed of the type comprising cholesterol oxidase, and a buffering agent in an amount to produce a solution having a pH of between about 5.5 and about 8, characterized in that said reagent further comprises means for neutralizing substantially all oxygen consumption inhibiting effects of inhibiting effects present in said sample to be assayed, said means consisting of alkyldimethylbenzylammonium salt in an amount sufficient to neutralize substantially all oxygen consumption inhibiting effects of inhibiting agents present in said sample to be assayed.

2. A freeze dried cholesterol assay enzymatic reagent, said freeze dried reagent prepared from the reagent of claim 1.

3. A cholesterol assay enzymatic reagent for rate determination of cholesterol in a sample to be assayed comprising:
   (a) from about 0.2 to about 5 International Units of cholesterol oxidase per milliliter of reagent;
   (b) from about 0 to about 5 International Units of cholesterol esterase per milliliter of reagent;
   (c) from about 0.01 to about 0.4 percent by weight of said reagent of an alkyldimethylbenzylammonium salt; and
   (d) a buffering agent in an amount to produce a solution having a pH of between about 5.5 and about 8.

4. The reagent of claim 3 wherein said alkyldimethylbenzylammonium salt is selected from a group consisting of alkyldimethylbenzylammonium chloride and mixtures thereof, wherein said alkyl moiety contains from 8 to 18 carbon atoms.

5. The reagent of claim 3 wherein said alkyldimethylbenzylammonium salt is a mixture comprising about 50% of sodium tetradecyldimethylbenzylammonium chloride, about 40% of sodium dodecyldimethylbenzylammonium chloride, and about 10% of sodium hexadecyldimethylbenzylammonium chloride.

6. A cholesterol assay enzymatic reagent for rate determination of cholesterol in a sample to be assayed comprising:
   (a) a buffering agent in an amount to produce a solution having a pH of about 6;
   (b) about 1.2 International Units of cholesterol oxidase per milliliter of reagent;
   (c) about 0.014 International Units of cholesterol esterase per milliliter of reagent;
   (d) about 0.08 percent by weight of said reagent of a bile salt;
   (e) about 0.05 percent by weight of said reagent of isooctylphenoxypolyethoxyethanol; and
   (f) about 0.1 percent by weight of said reagent of an alkyldimethylbenzylammonium salt.

7. The reagent of claim 6 wherein said alkyldimethylbenzylammonium salt is a mixture comprising about 50% of sodium tetradecyldimethylbenzylammonium chloride, about 40% of sodium dodecyldimethylbenzylammonium chloride, and about 10% of sodium hexadecyldimethylbenzylammonium chloride.

8. In a cholesterol assay enzymatic reagent kit capable of being employed for rate determination of cholesterol in a sample to be assayed of the type comprising:
   (a) a first reagent comprising:
      (i) cholesterol esterase and
      (ii) cholesterol oxidase; and
   (b) a second reagent comprising:
      (i) a buffer solution having a pH of between about 5.5 to about 8;
said reagents adapted to be employed together; the improvement being that said second reagent further comprises means for neutralizing substantially all oxygen consumption inhibiting effects of inhibiting agents present in said sample to be assayed, said means consisting of an alkyldimethylbenzylammonium salt in an amount sufficient to neutralize substantially all oxygen consumption inhibiting effects of inhibiting agents present in said sample to be assayed.

9. In a cholesterol assay enzymatic reagent kit capable of being employed for rate determination of cholesterol in a sample to be assayed of the type comprising:
   (a) a first reagent comprising cholesterol esterase;
   (b) a second reagent comprising cholesterol oxidase; and
   (c) a third reagent comprising a buffering solution having a pH of from about 5.5 to about 8;
said reagents adapted to be employed together; the improvement being that said third reagent further comprises a means for neutralizing substantially all oxygen consumption inhibiting effects of inhibiting agents present in said sample to be assayed, said means consisting of an alkyldimethylbenzylammonium salt in an amount sufficient to neutralize substantially all oxygen consumption inhibiting of inhibiting agents present in said sample to be assayed.

10. A cholesterol assay enzymatic reagent kit capable of being employed for rate determination of cholesterol in a sample to be assayed comprising, base upon a combined solution of a first reagent comprising cholesterol esterase; a second reagent comprising cholesterol oxidase; and a third reagent comprising a buffer solution having a pH of about 6, a bile salt, and a non-ionic surfactant, said reagents adapted to be employed together:
   (a) an aqueous solution of potassium orthophosphate in an amount to produce a solution having a pH of about 6;
   (b) about 0.08 percent by weight of said combined solution of sodium cholate;
   (c) about 0.05 percent by weight of said combined solution of isooctylphenoxypolyethanol;
   (d) about 0.1 percent by weight of said combined solution of an alkyldimethylbenzylammonium salt;
   (e) about 1.2 International Units of cholesterol oxidase per milliliter of said combined solution;
   (f) about 0.014 International Units of cholesterol esterase per milliliter of said combined solution.

11. The reagent kit of claim 10 wherein said alkyldimethylbenzylammonium salt is a mixture comprising about 50% of sodium tetradecyldimethylbenzylammonium chloride, about 40% of sodium dodecyldimethylbenzylammonium chloride, and about 10% of sodium hexadecyldimethylbenzylammonium chloride.

12. In a rate method for determining the cholesterol concentration in a cholesterol containing sample comprising the steps of:
   (a) oxidizing the cholesterol present in the sample in an oxygen saturated aqueous solution by means of a cholesterol assay enzymatic reagent of the type comprising:
      (i) cholesterol oxidase and;
      (ii) a buffering agent in an amount to produce a solution having a pH of between 5.5 and about 8; in the presence of a sensor which serves to monitor a property or characteristic of oxygen in said solution related to the oxygen concentration thereof;

(b) generating a first electrical signal related to said oxygen concentration;

(c) differentiating said first electrical signal to produce an output signal proportional to the instantaneous time rate of change of oxygen concentration; and (d) measuring said output signal to determine said cholesterol concentration; the improvement comprising neutralizing substantially all oxygen consumption inhibiting effects of inhibiting agents in said sample to be assayed by including in said cholesterol assay enzymatic reagent a cationic surfactant in an amount sufficient to neutralize substantially all oxygen consumption inhibiting effects of inhibiting agents present in said sample to be assayed.

13. The method of claim 12 wherein said reagent further comprises cholesterol esterase.

14. The method of claim 13 wherein said reagent comprises:
(a) from about 0.2 to about 5 International Units of cholesterol oxidase per milliliter of reagent;
(b) from about 0 to about 5 International Units of cholesterol esterase per milliliter of reagent; and
(c) from about 0.01 to about 0.4 percent by weight of said reagent of said cationic surfactant.

15. The method of claim 14 wherein said cationic surfactant is selected from a group consisting of quanternary imidazolinium, pyridinium, quinolinium and quanternary ammonium surfactants.

16. The method of claim 15 wherein said cationic surfactant is a quanternary ammonium surfactant.

17. The method of claim 16 wherein said cationic quanternary ammonium surfactant is an alkyldimethylbenzylammonium salt.

18. The method of claim 17 wherein said alkyldimethylbenzylammonium salt is selected from a group consisting of alkyldimethylbenzylammonium chloride and mixtures thereof, wherein said alkyl moeity contains from 8 to 18 carbon atoms.

19. The method of claim 17 wherein said alkyldimethylbenzylammonium salt is a mixture comprising about 50% of sodium tetradecyldimethylbenzylammonium chloride, about 40% of sodium dodecyldimethylbenzylammonium chloride, and about 10% of sodium hexadecyldimethylbenzylammonium chloride.

20. The method of claim 14 wherein said reagent further comprises a bile salt an a non-ionic surfactant.

21. The method of claim 20 wherein said reagent comprises from about 0.01 to about 0.1 percent by weight of said reagent of said bile salt and from about 0.05 to about 0.4 percent by weight of said reagent of said non-ionic surfactant.

22. The method of claim 21 wherein said reagent comprises:
(a) said buffering agent in an amount to produce a solution having a pH of about 6;
(b) about 1.2 International Units of cholesterol oxidase per milliliter of reagent;
(c) about 0.014 International Units of cholesterol esterase per milliliter of reagent;
(d) about 0.08 percent by weight of said reagent by said bile salt;
(e) about 0.05 percent by weight of said reagent of isooctyloxypolyethoxyethanol; and
(f) about 0.1 percent by weight of said reagent of an alkyldimethylbenzylammonium salt.

23. The method of claim 22 wherein said alkyldimethylammonium salt is a mixture comprising about 50% of sodium tetradecyldimethylbenzylammonium chloride, about 40% of sodium dodecyldimethylbenzylammonium chloride, and about 10% of sodium hexadecyldimethylbenzylammonium chloride.

24. In a method of determining the cholesterol concentration in a cholesterol containing sample comprising the steps of:
(a) oxidizing the cholesterol present in the sample in an oxygen saturated aqueous solution by means of a cholesterol assay enzymatic reagent of the type comprising:
  (i) cholesterol oxidase; and
  (ii) a buffering agent in an amount to produce a solution having a pH of between about 5.5 and about 8 in the presence of a sensor which serves to monitor a property or characteristic of oxygen in said solution related to the oxygen concentration thereof;
(b) generating a first electrical signal related to said oxygen concentration;
(c) differentiating said first electrical signal to produce an output signal proportional to the instantaneous time rate of change of oxygen concentration; and
(d) measuring said output signal to determine said cholesterol concentration;

the improvement comprising neutralizing substantially all oxygen consumption inhibiting effects of inhibiting agents in said sample to be assayed by including in said cholesterol assay enzymatic reagent from about 0.01 to about 0.4 percent by weight of said reagent of a cationic surfactant.

25. The method of claim 24 wherein said reagent further comprises cholesterol esterase.

26. The method of claim 25 wherein said cationic surfactant is an alkyldimethylammonium salt.

27. The method of claim 26 wherein said reagent further comprises a bile salt and a nonionic surfactant.

* * * * *